(12) United States Patent
Gregorski

(10) Patent No.: US 9,448,185 B2
(45) Date of Patent: Sep. 20, 2016

(54) SYSTEM AND METHOD FOR INSPECTING A BODY

(71) Applicant: Corning Incorporated, Corning, NY (US)

(72) Inventor: Steven Joseph Gregorski, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/288,790

(22) Filed: May 28, 2014

(65) Prior Publication Data

US 2015/0346114 A1 Dec. 3, 2015

(51) Int. Cl.
G01N 21/00 (2006.01)
G01N 21/954 (2006.01)
G01N 21/956 (2006.01)

(52) U.S. Cl.
CPC ...... *G01N 21/954* (2013.01); *G01N 21/95692* (2013.01)

(58) Field of Classification Search
CPC ......... G01N 21/00; H04N 7/18; F21S 48/24; G06F 3/14; H01S 3/00; G03B 21/14
See application file for complete search history.

(56) References Cited

U.S. PATENT DOCUMENTS

| | | | |
|---|---|---|---|
| 3,932,859 A * | 1/1976 | Kyriakides et al. | .......... 345/171 |
| 7,366,340 B1 | 4/2008 | Smithgall | |
| 8,234,909 B2 | 8/2012 | Suman et al. | |
| 8,421,857 B2 | 4/2013 | Akao et al. | |
| 8,421,860 B2 | 4/2013 | Akao et al. | |
| 2003/0081202 A1 | 5/2003 | Yoneda | |
| 2003/0174320 A1 | 9/2003 | Yokoyama et al. | |
| 2007/0091309 A1 | 4/2007 | Kondo | |
| 2010/0045975 A1 | 2/2010 | Zoeller, III | |
| 2010/0238284 A1* | 9/2010 | Akao et al. | .................... 348/135 |
| 2013/0162955 A1* | 6/2013 | Okamoto et al. | ............... 353/30 |
| 2014/0226354 A1* | 8/2014 | Mugge | .......................... 362/511 |

FOREIGN PATENT DOCUMENTS

| | | |
|---|---|---|
| CN | 102735191 | 10/2012 |
| EP | 0624788 | 11/1994 |

(Continued)

OTHER PUBLICATIONS

The International Search Report and The Written Opinion of the International Searching Authority, International Filing Date May 28, 2015, International Application No. PCT/US2015/032776.

*Primary Examiner* — Tarifur Chowdhury
*Assistant Examiner* — Jamil Ahmed
(74) *Attorney, Agent, or Firm* — Charles A. Greene

(57) ABSTRACT

A system for inspecting a body, which includes a first end side, a second end side, and cells extending through the body from the first end side to the second end side, is provided. The system includes at least one light source configured to project light through and out of at least one corresponding group of the cells, a target configured to display the light projected through and out of the at least one corresponding group of the cells, an imaging system configured to determine at least one location of the displayed light on the target, and a system processor configured to compare the determined at least one location of the displayed light with a location of the at least one light source and calculate, from the comparison thereof, at least one of a pointing angle and a pointing vector for the at least one corresponding group of the cells.

20 Claims, 12 Drawing Sheets

(56) References Cited

FOREIGN PATENT DOCUMENTS

| JP | S56-107148 A | 8/1981 |
| JP | 1992043767 | 10/1992 |
| JP | H05-264459 A | 10/1993 |
| JP | H06-43114 A | 2/1994 |
| JP | 2002-243650 A | 8/2002 |
| JP | 2013173243 | 9/2013 |
| WO | 20130125483 A1 | 8/2013 |

* cited by examiner

SYSTEM AND METHOD FOR INSPECTING A BODY

FIELD

The following description relates generally to a system and a method for inspecting a body.

BACKGROUND

A body, in the form of a body having cells extending there through, can be used in collecting undesirable fine particles associated with the operation of vehicle engines and/or other environmental applications. A forming of the body includes a forming of the cells inside the body longitudinally from one side of the body to another and a firing of the body. After the body is fired, the body may be skinned in preparation for use in industrial applications.

SUMMARY

The following presents a simplified summary of the disclosure in order to provide a basic understanding of some example aspects described in the detailed description.

In a first aspect, a system for inspecting a body is provided. The body includes a first end side, a second end side, and cells extending through the body from the first end side to the second end side. The system includes at least one light source configured to project light through and out of at least one corresponding group of the cells, a target configured to display the light projected through and out of the at least one corresponding group of the cells, an imaging system configured to determine at least one location of the displayed light on the target, and a system processor configured to compare the determined at least one location of the displayed light with a location of the at least one light source and calculate, from the comparison thereof, at least one of a pointing angle and a pointing vector for the at least one corresponding group of the cells.

In one example of the first aspect, the at least one light source is a diffuse light source.

In another example of the first aspect, the target is one of semi-transparent and opaque.

In still another example of the first aspect, the imaging system is further configured to gather data related to a surface of the target and determine a location of a centroid of the displayed light from the gathered data.

In still yet another example of the first aspect, the system processor is further configured to compare the determined location of the centroid with the location of the at least one light source and calculate, from the comparison thereof, the at least one of the pointing angle and the pointing vector for the at least one corresponding group of the cells.

In yet another example of the first aspect, the imaging system includes a digital imaging sensor.

In a further example of the first aspect, the at least one light source is one of multiple light sources configured to project light through and out of multiple corresponding groups of the cells. The at least one corresponding group of the cells is one of the multiple corresponding groups of the cells. In this example, the target is further configured to display the light projected through and out of the multiple corresponding groups of the cells. In this example, the imaging system is further configured to determine multiple locations of the displayed light on the target. The at least one location of the displayed light on the target is one of the multiple locations of the displayed light on the target. In this example, the system processor is further configured to compare the determined multiple locations of the displayed light with respective locations of the multiple light sources and calculate, from the comparison thereof, at least one of the pointing angle and the pointing vector for the multiple corresponding groups of the cells.

In a yet further example of the first aspect, the multiple light sources are further configured to project the light simultaneously.

In another example of the first aspect, after the system processor calculates the at least one of the pointing angle and the pointing vector for the at least one corresponding group of the cells, the at least one light source is moved to project light through and out of another corresponding group of the cells.

The first aspect may be provided alone or in combination with one or any combination of the examples of the first aspect discussed above.

In a second aspect, a method for inspecting a body is provided. The body includes a first end side, a second end side, and cells extending through the body from the first end side to the second end side. The method includes projecting light through and out of at least one group of the cells from at least one corresponding light source, displaying the light projected through and out of the at least one group of the cells, determining at least one location of the displayed light, comparing the determined at least one location of the displayed light with a location of the least one corresponding light source projecting the light, and calculating, from the location comparison thereof, at least one of a pointing angle and a pointing vector for each of the at least one group of the cells.

In one example of the second aspect, the projecting of the light includes projecting diffuse light.

In another example of the second aspect, the displaying of the light includes displaying the light on a target that is one of semi-transparent and opaque.

In still another example of the second aspect, the displaying of the light includes displaying the light on a target. The determining of the at least one location includes gathering data related to a surface of the target and determining a location of a centroid of the displayed light from the gathered data.

In yet still another example of the second aspect, the comparing of the locations includes comparing the determined location of the centroid with the location of the at least one corresponding light source. The calculating of the at least one of the pointing angle and the pointing vector includes calculating, from the comparing of the determined location of the centroid with the location of the at least one corresponding light source, the at least one of the pointing angle and the pointing vector for the at least one group of the cells.

In yet still another example of the second aspect, the determining of the at least location is performed by a digital imaging sensor.

In a further example of the second aspect, the projecting of the light includes projecting the light through and out of multiple groups of the cells from multiple corresponding light sources. The at least one group of the cells is one of the multiple groups of the cells. The at least one corresponding light source is one of the multiple corresponding light sources. The displaying of the light includes displaying the light projected through and out of the multiple groups of the cells. The determining of the at least one location includes determining multiple locations of the displayed light. The at least one location of the light is one of the multiple locations of the displayed light. The comparing of the determined at least one location includes comparing the determined multiple locations of the displayed light with locations of the multiple corresponding light sources. The calculating includes calculating, from the location comparison thereof, at least one of the pointing angle and the pointing vector for the multiple groups of the cells.

In another example of the second aspect, the projecting of the light through and out of two or more of the groups of the cells is simultaneous.

In yet another example of the second aspect, the method further includes, after the calculating of the at least one of the pointing angle and the pointing vector, moving the at least one corresponding light source and repeating the projecting, the displaying, the determining, the comparing, and the calculating for another group of the cells.

The second aspect may be provided alone or in combination with one or any combination of the examples of the second aspect discussed above.

In a third aspect, a system for inspecting a body is provided. The body includes a first end side, a second end side, and cells extending through the body from the first end side to the second end side. The system includes comprises multiple light sources configured to simultaneously project light through and out of multiple corresponding groups of the cells, a target configured to display the light simultaneously projected through and out of the multiple corresponding groups of the cells in multiple regions respectively corresponding with the multiple groups of the cells, an imaging system configured to determine respective centroids of the multiple regions, and a system processor configured to compare locations of the respective centroids of the multiple regions with respective locations of the multiple light sources and calculate, from the comparison thereof, at least one of a pointing angle and a pointing vector for the multiple corresponding groups of the cells.

In another example of the third aspect, the imaging system includes an imaging device includes a digital imaging sensor. The imaging device is configured to gather data from a surface of the target facing the multiple corresponding groups of the cells.

The third aspect may be provided alone or in combination with one or any combination of the examples of the third aspect discussed above.

BRIEF DESCRIPTION OF THE DRAWINGS

These and other features, aspects and advantages of the present disclosure are better understood when the following detailed description is read with reference to the accompanying drawings, in which.

DETAILED DESCRIPTION

Figure 1:
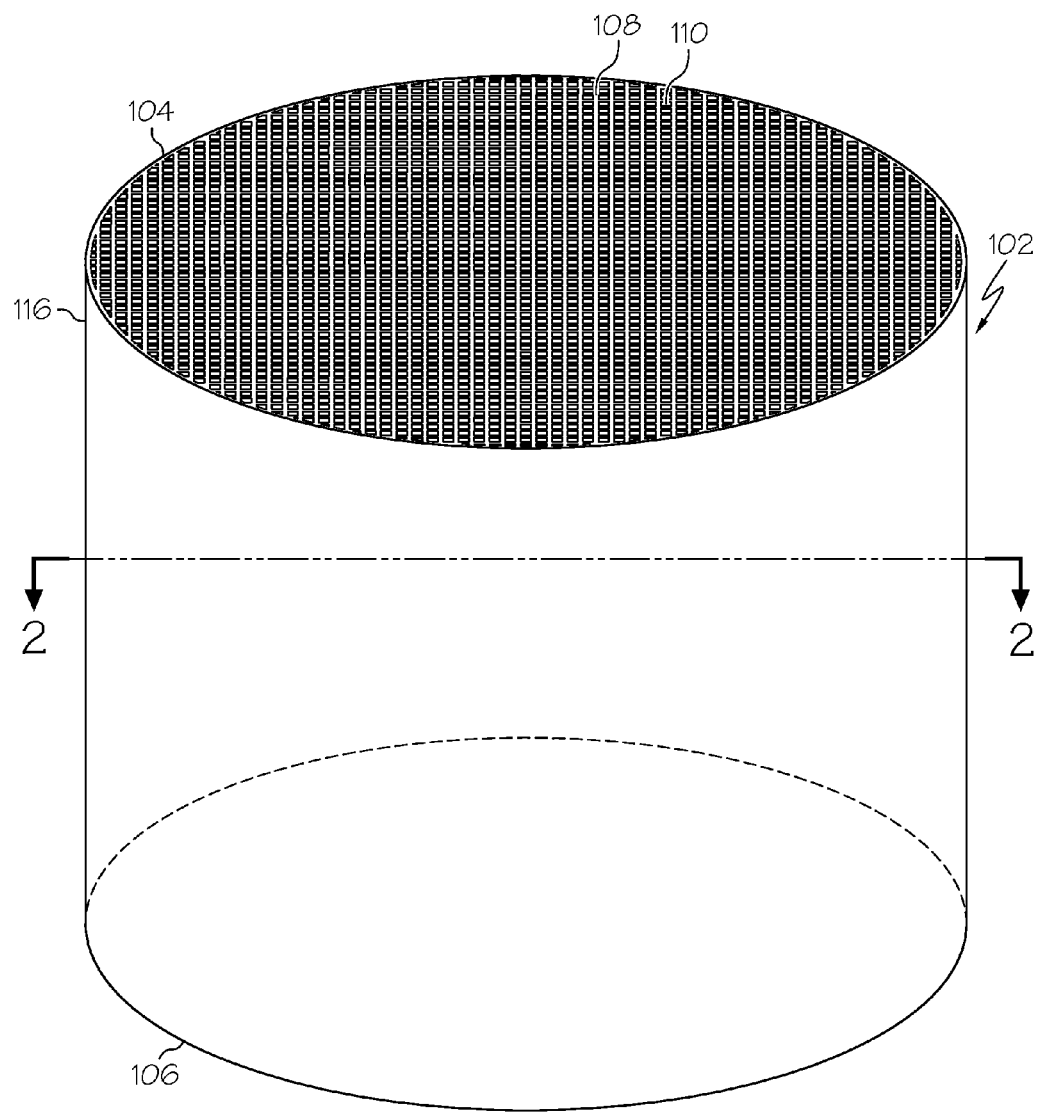
FIG. 1 is a perspective view illustrating an example of a body in accordance with an embodiment.
Figure 2:
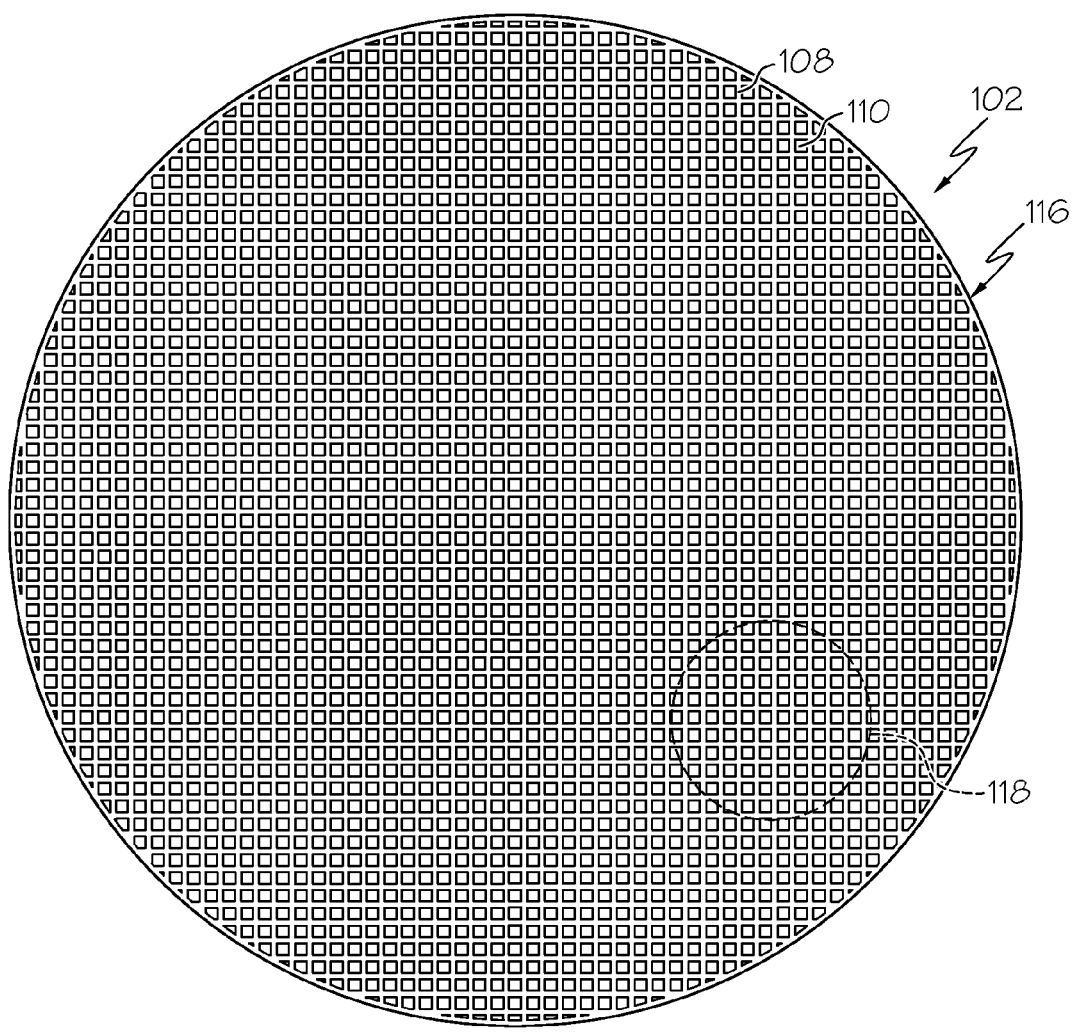
FIG. 2 is a schematic sectional view illustrating an example of the body of FIG. 1 along line 2-2 in accordance with an embodiment.

Examples will now be described more fully hereinafter with reference to the accompanying drawings in which example embodiments are shown. Whenever possible, the same reference numerals are used throughout the drawings to refer to the same or like parts. However, aspects may be embodied in many different forms and should not be construed as limited to the embodiments set forth herein.

The terminology used herein is for describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the examples illustrated in FIGS. 1-11, a system for inspecting a body 102 is described. The body 102 may include a first end side 104, a second end side 106, and cells 110 extending through the body 102 from the first end side 104 to the second end side 106. The system may include at least one light source 124, a target 136, an imaging system 160, and a system processor 166.

The body 102 may include a plurality of intersecting walls 108 defining a network of cells 110 that extend through the body 102 between a first end side 104 and a second end side 106 positioned opposite from the first end side 104. The intersecting walls 108 and the cells 110 may extend longitudinally between the first end side 104 and the second end side 106 of the body 102. The body 102 may include an outer surface 116 that extends longitudinally between the first end side 104 and second end side 106.

In an example, the body 102 can include at least one of cordierite, mullite, alumina, silicon carbide, zirconia, corundum, corundum-mullite, and aluminum titanate, but is not limited thereto.

In an example, the body 102 may be a honeycomb ceramic body to be used as a particulate filter with the operation of vehicle engines or other environmental applications. The network of cells 110 may also be a honeycomb network. However, embodiments described herein are not limited thereto. For example, various geometries may be incorporated in accordance with various example embodiments. The body 102 can include a rectangular (e.g., square) cross-sectional outer periphery or other polygonal shape having three or more sides. Further, the body 102 can include an outer cross-sectional periphery that is circular, oval, or another curved shape.

In an example, the outer surface 116 may include a circular cylindrical shape having a circular cross-sectional profile. However, embodiments disclosed herein are not limited thereto. For example, the outer surface 116 of the body 102 can have an elliptical, polygonal, or other shape. Further, the polygonal shape can be a triangular, rectangular (e.g., square), or other polygonal shape.

Figure 3:
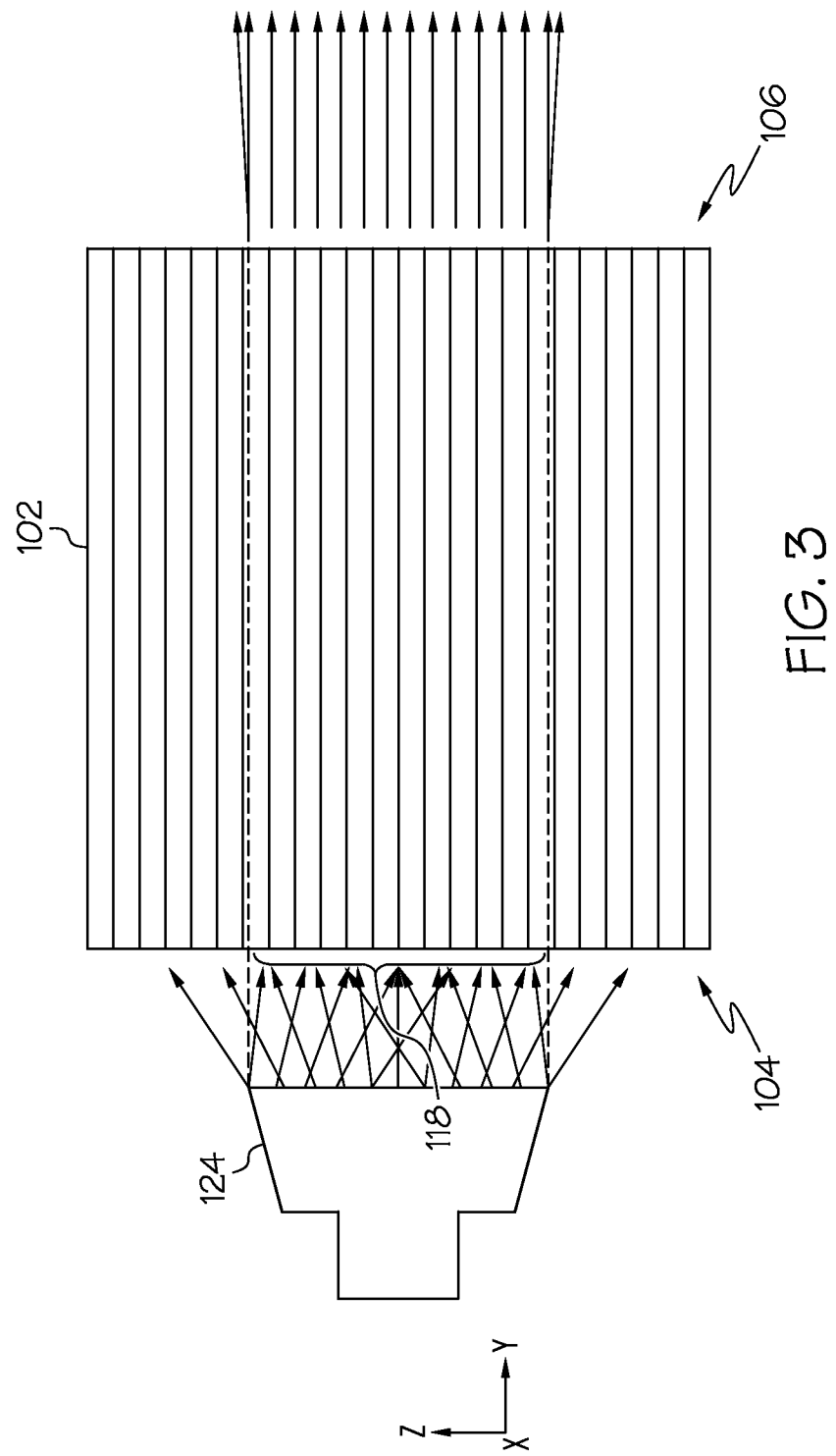
FIG. 3 is a schematic side view illustrating an example of a light source projecting light through and out of a body in accordance with an embodiment.
Figure 4:
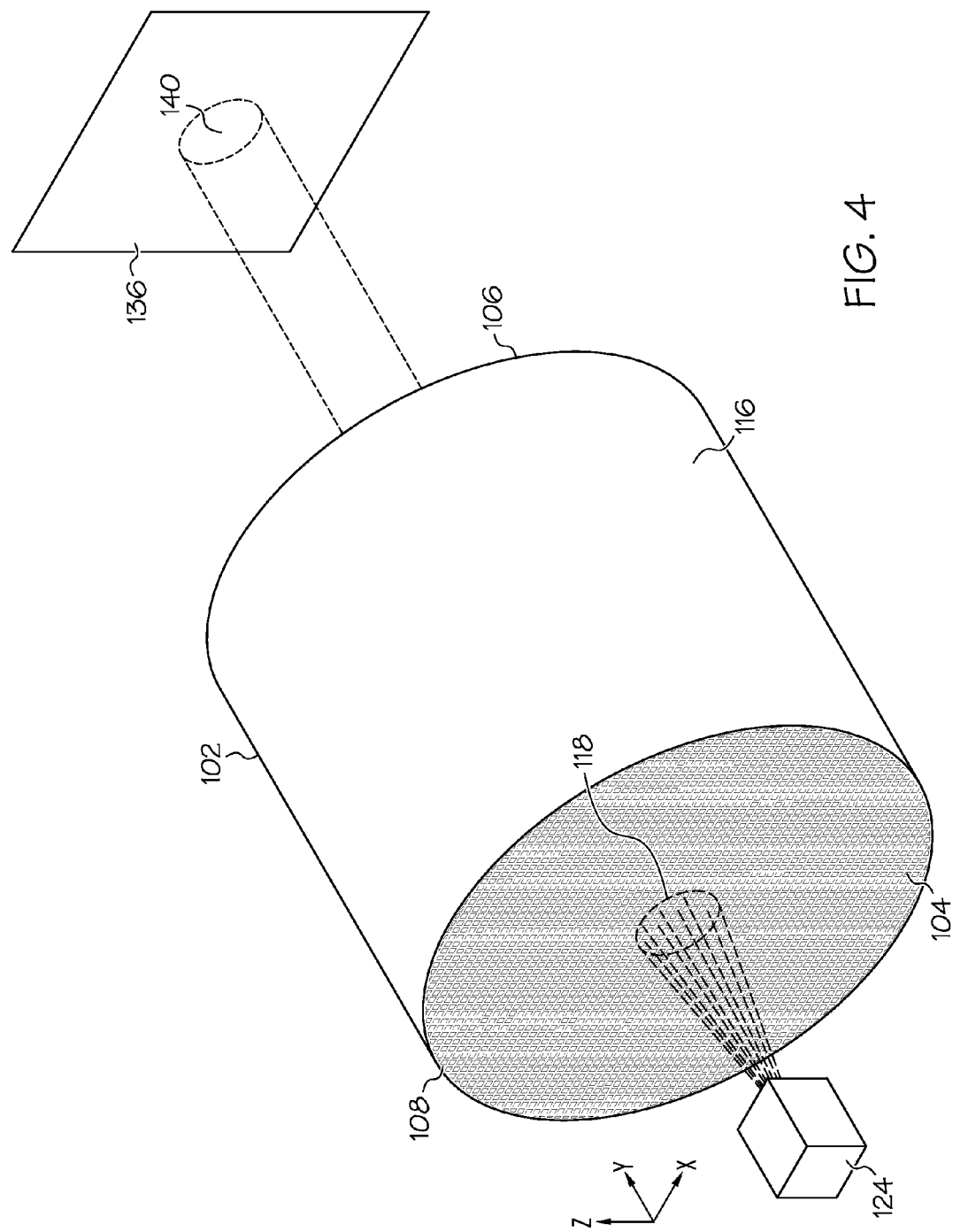
FIG. 4 is a schematic perspective view illustrating an example of a light source projecting light through and out of a corresponding group of cells of a body in accordance with an embodiment.
Figure 5:
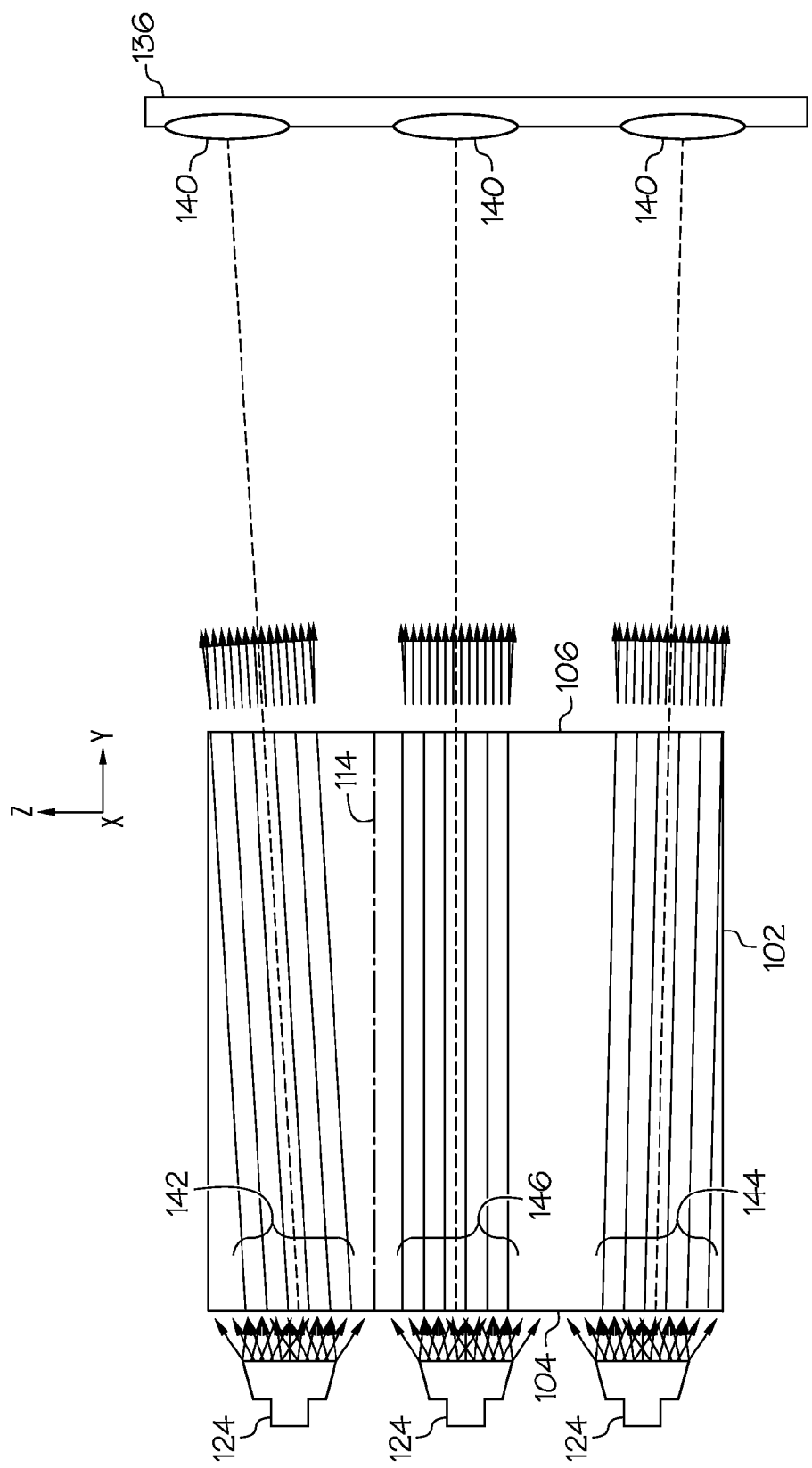
FIG. 5 is a schematic side view illustrating an example of light sources projecting light through and out of corresponding groups of cells of a body onto a target in accordance with an embodiment.

As illustrated, at least one light source 124 of the system may project light through and out of at least one corresponding group 118 of the cells 110. In the examples illustrated, the light source 124 may be a diffuse light source emitting diffuse light. While only one light source 124 is illustrated in FIG. 3, embodiments herein are not limited thereto, as is illustrated by FIGS. 5-7 and 9-12, where multiple light sources 124 are illustrated that can be used to inspect the body 102. In situations where multiple light sources 124 project light through and out of multiple corresponding groups 118 of the cells 110, the light sources 124 may operate simultaneously to project the light through the multiple corresponding groups 118 of the cells 110 at the same time.

Light from the diffuse light source 124 can be provided at many non-parallel angles to a group 118 of the cells 110 of the body 102. A variety of different types of diffuse light sources, including, but not limited to, laser-producing light sources, incandescent light sources, or light-emitting diode (LED) light sources, can be used.

The light source 124 can define a size and shape of the corresponding group 118 of the cells 110. The shape and size of the group 118 of the cells 110 can correspond with a shape and size of the light source 124, as well as a way in which the light source 124 emits light. Further, the nature of beams of light projecting through and out of the body 102 may be different from the nature of beams of light projected to the group 118 of the cells 110. For example, light emitted from the light source 124 as diffuse light can be projected through and out of the group 118 of the cells 110 of the body 102 as quasi-collimated light including beams of light that are slightly divergent or convergent. For example, quasi-collimated light can be divergent or convergent over an angular range of no more than about 5 degrees. The cells 110 of the body 102 can serve to collimate the light being emitted from the light source 124 according to the group 118 of the cells 110 through which the light is projected through and out of.

The light source 124 can be spaced from and positioned adjacent to the first end side 104 of the body 102 by a predetermined distance for projecting the light through and out of the group 118 of the cells 110 of the body 102. In one example, the light source 124 can be away from the body 102 by a distance from about 0.1 cm to about 10 cm.

The light source 124 can also be positioned such that the light source 124 is aligned with a longitudinal axis 114 of the body 102. An example of the longitudinal axis 114 of the body 102 is illustrated in FIGS. 5 and 9-11. In one example, the longitudinal axis 114 of the body 102 is an axis nominally perpendicular to the first end side 104 of the body 102 and the second end side 106 of the body.

Both the light source 124 and the body 102 can be configured to be stationary with respect to each other during the inspection of the body 102. Alternatively, as shown in an example illustrated in FIG. 8, at least one of the light source 124 and the body 102 may be configured to be movable with respect to each other. In one non-limiting example, the light source 124 can be configured to move in at least one of x, y and z direction by a predetermined distance to provide light to a corresponding group 118 of the cells 110 of the body 102.

The target 136 of the system may display the light projected through and out of the corresponding group or groups 118 of the cells 110. The target 126 may be semi-transparent or opaque, depending how the system is configured to collect data, to distinguish the light 140 displayed on the target 136 from the remaining portion of the target 136.

The target 136 can be positioned at an opposite side of the body 102 from the light source 124 with respect to the body 102. The target 136 can be spaced a predetermined distance from the body 102. For example, the target 136 can be spaced from the body 102 by a distance ranging from about 0.25 m to about 5 m. The target 136 can be flat.

As discussed above, light from the light source 124 projected through and out of the corresponding group 118 of the cells 110 can be quasi-collimated light corresponding with the orientation of the cells 110 belonging to the group 118. As such, beams projected out of the corresponding group 118 of the cells 110 may be sized differently from the displayed light 140 on the target 136. A shape of light 140 displayed on the target 136 can depend on a shape of the light source 124. For example, the shape of the displayed light 140 can have a circular orientation for a light source 124 that has a circular orientation. The orientation of the light source 124 is not limited to being circular and can be dependent on the type and shape of a light source being implemented in the system.

In the examples illustrated in FIGS. 5 and 9-11, the body 102 includes multiple groups 142, 144, 146 of the cells 110 that can be in a non-parallel relationship with respect to the longitudinal axis 114 of the body 102. As illustrated, in comparison with the group 144 of the cells 110 located near a lower outer periphery of the body 102, the group 142 of the cells 110 located near an upper outer periphery of the body 102 is tilted with respect to the longitudinal axis 114. In this example, the group 146 of the cells 118 located near the center of the body 102 is substantially parallel to the longitudinal axis 114.

While the multiple groups 142, 144, 146 of the cells 110 illustrated in FIGS. 5 and 9-11 are shown in a particular arrangement, embodiments disclosed herein are not intended to be limiting. In one example, the cells 146 located near the lower outer periphery of the body 102 can be more tilted, compared to the cells 142 located near the upper outer periphery of the body 102. Further, the system may operate with the expectation that each body that is presented for inspection may have a unique cellular relationship leading to unique results for each body.

Multiple light sources 124 are illustrated in FIGS. 5 and 9-11 for projecting light through and out of the multiple groups 142, 144, 146 of the cells 110, each of the multiple groups 142, 144, 146 of the cells 110 corresponding respectively with one of the multiple light sources 124 of the body 102. In one example, the light sources 124 may be stationary at all times and simultaneously emit light to be projected through and out of the cells 110. In another example, the light sources 124 can move in at least one of x, y, and z directions by a predetermined distance to project light through and out of different groups of the cells 110.

The light sources 124 can each be configured to emit light having a particular color that can be the same as or different from the color of light being emitted from other light sources 124. For example, one light source 124 can project yellow-colored light while another light source 124 can simultaneously project red-colored light, and so on. In each case, the particular color of the light being projected by the light sources 124 through and out of the corresponding groups 118 of the cells 110 will be displayed accordingly in the light 140 on the target 136.

In the operation according to the example illustrated in FIGS. 5 and 9-11, the light from the corresponding light sources 124 projects through and out of the groups 142, 144, 146 of the cells 110 can be displayed on the target 136. The target 136 can display the projected beams of light 140 simultaneously on the target 136. Alternately, the respective projected beams of light can be configured to be sequentially displayed one at a time on the target 136. As illustrated, for the groups 142, 144 of the cells 110 located near the upper and/or lower outer periphery of the body 102, the beams of light projected through and out thereof can also be tilted with respect to the longitudinal axis 114 of the body 102. As such, the locations of the displayed light 140 for the tilted groups 142, 144 of the cells 110 on the target 136 can deviate from positions of corresponding light sources 124. While FIGS. 5 and 9-11 illustrate the tilt of the projected beams of light for the groups 142, 144 of the cells 110 only in the z direction, it is not intended to be limiting as the tilting of for the groups 142, 144 of the cells 110 in FIGS. 5 and 9-11 can also be, for example, in the x and z directions.

Figure 6:
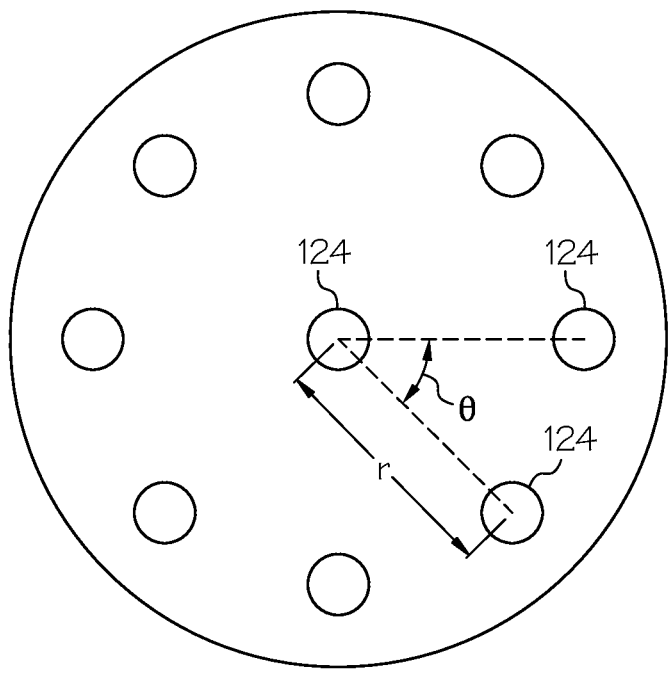
FIG. 6 is a schematic view illustrating an example of an arrangement of light sources in accordance with an embodiment.

In the example illustrated in FIG. 6, the light sources 124 can be arranged in a ring shape corresponding to an outer region of the first end side 104 of the body 102 to project light through and out of corresponding groups 118 of the cells 110. The light sources 124 can be spaced accordingly to form the ring shape corresponding to an outer region of the first end side 104 of the body 102. An additional light source 124 can be also positioned corresponding to a center region of the first end side 104 of the body 102 to project light through and out of a corresponding group 118 of the cells 110.

The positions of the light sources 124 can be represented by the polar coordinate system, which, in the example illustrated in FIG. 6, is based on a distances (r) between the light source 124 corresponding to the center region of the first end side 104 and light sources 124 corresponding to adjacent outer regions of the first end side 104 and an angular angle (θ) between the light sources 124 corresponding to the adjacent outer regions of the first end side 104.

Figure 7:
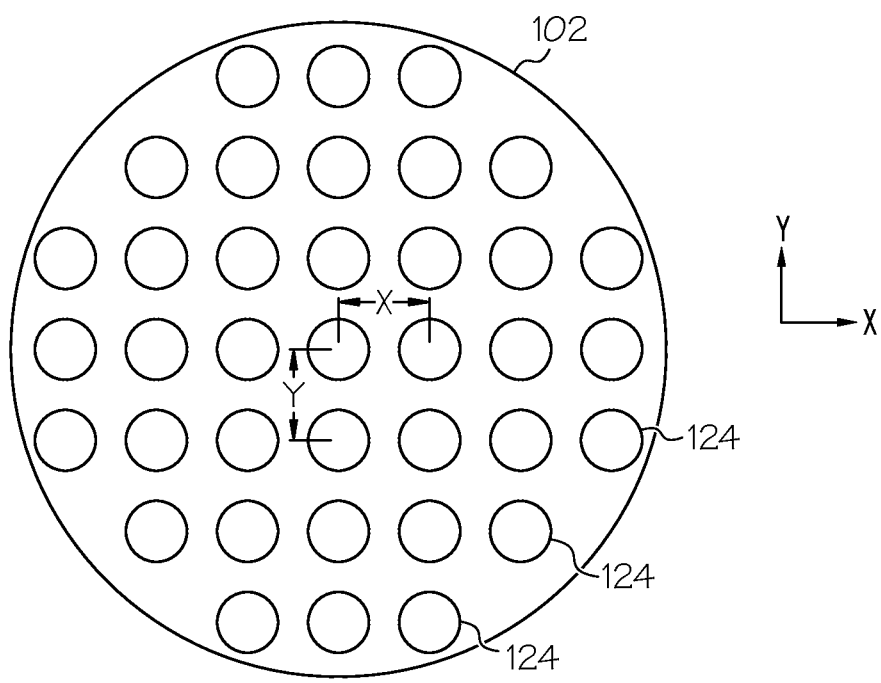
FIG. 7 is a schematic view illustrating another example of an arrangement of light sources in accordance with an embodiment.

Alternately, as in the example illustrated in FIG. 7, positions of the light sources 124 with respect to each other can be represented by the Cartesian coordinate system, where the location of one light source 124 according to another adjacent light source 124 can be represented by the distance in both x and/or y directions between the light sources 124. In the example illustrated in FIG. 7, each light source 124 is arranged in a grid pattern with a gap of X and Y in respective x and y directions between adjacent light sources 124. Further, in the example illustrated in FIG. 7, the light sources 124 can be arranged such that the displayed light 140 projected through and out of the corresponding groups 118 of the cells 110 does not overlap each other on the target 136. Arrangements illustrated in FIGS. 6 and 7 are not intended to be limiting, as the light sources 124 can be arranged in a variety of different arrangements.

Figure 8:
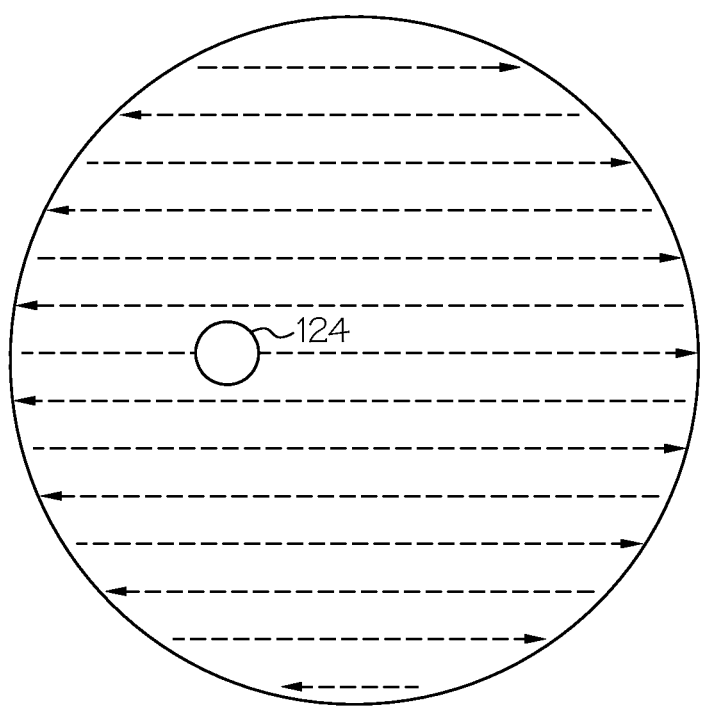
FIG. 8 is a schematic view illustrating an example of a movable light source enabling a system to make multiple discrete inspections of a body in accordance with an embodiment.

FIG. 8 illustrates an example in which only one light source 124 projects light through and out of a group 118 of the cells 110 of the body 102, but can be moved in order to project light through and out of another group 118 of the cells 110 after determining a location of the light 140 displayed on the target 136 corresponding with the initial group 118 of the cells 110. The movable light source 124 can move in x and/or y directions along a predetermined path to a second position. As such, the light source 124 can sequentially project beams of light through and out of multiple groups 118 of cells 110, as opposed to FIGS. 6 and 7 where the light sources 124 are stationary and project beams of light through and out of the corresponding group 118 of the cells 110 only. As illustrated in FIG. 8, the movable light source 124 can follow a raster scan path. In other examples, the movable light source 124 can follow concentric circle or spiral paths. The light source 124 may be mechanically moved using a two-axis stage system or any other robotic, pneumatic, hydraulic, or electronic system known by one having ordinary skill in the art to be used to mechanically move items such as the light source 124.

Figure 9:
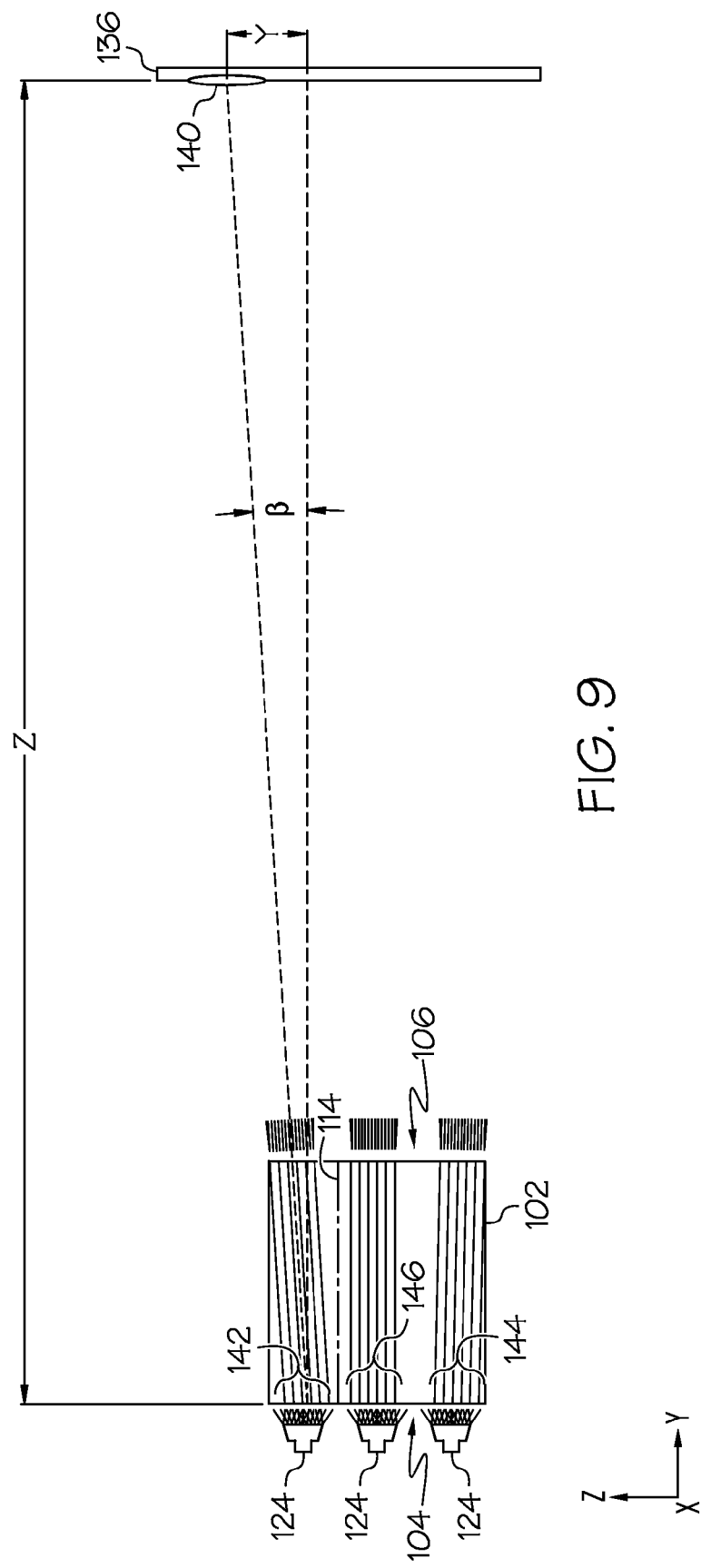
FIG. 9 is a schematic view illustrating an example of a relationship between a position of a light source and a position at which light from the light source is projected through and out of a corresponding group of cells of a body onto a target in accordance with an embodiment.

FIG. 9 illustrates an example relationship that may be determined through use of the system of inspection, in which the location of the light source 124 and the location of the corresponding light 140 displayed on the target 136 is compared to calculate at least one of the pointing angle and the pointing vector for a corresponding group 142 of the cells 110. The light sources 124 illustrated in this example emit diffuse light for projecting through and out of the corresponding groups 142, 144, 146 of cells 110. Quasi-collimated light may be projected out of the corresponding groups 142, 144, 146 of cells 110 and displayed on the target 136 to form displayed light 140. For the group 142 of the cells 110 that is not parallel with the longitudinal axis 114 of the body 102, the location of the displayed light 140 on the target 136 may deviate from the location of the corresponding light source 124.

In the example illustrated in FIG. 9, a cell angle (β) can be defined to represent the tilt of the group 142 of the cells 110 by comparing the determined location of the displayed light 140 with the location of the corresponding light source 124. For example, as is illustrated in FIG. 9, the cell angle (β) is the angle between a pointing vector of the group 142 of the cells 110 and the position of the light source 124 and a vector indicating a distance (Z) between the first end side 104 of the body and the target 136.

Figure 12:
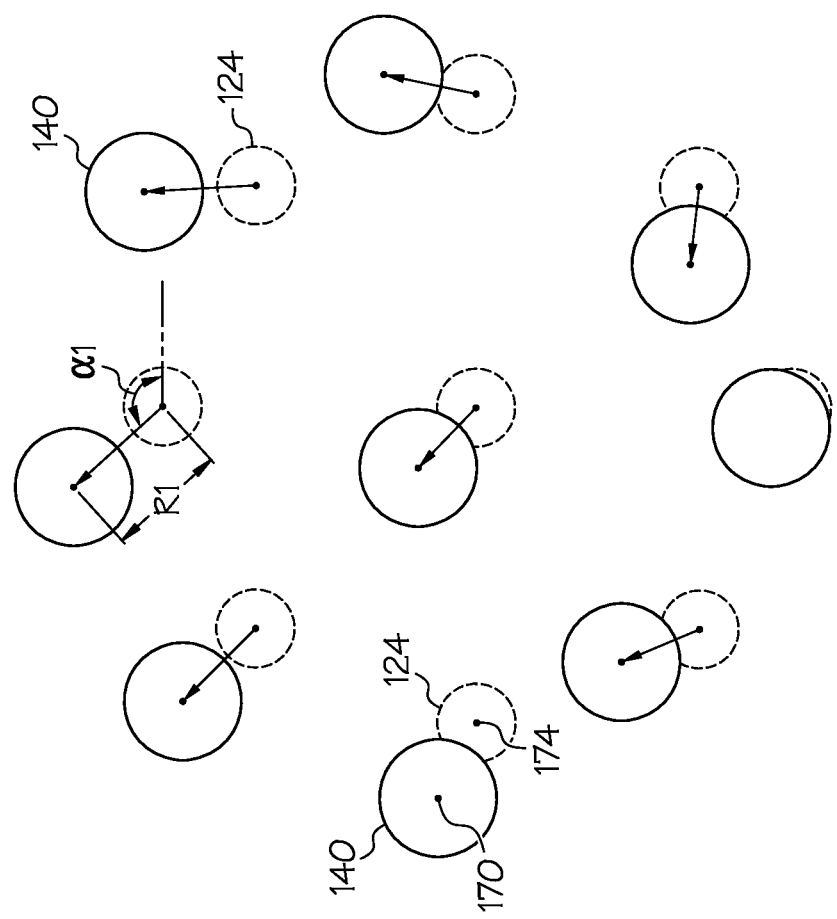
FIG. 12 is a schematic view illustrating positions of light sources and respective positions of light displayed on a target corresponding with the light sources in accordance with an embodiment.

The determination of the distance (Z) enables a calculation of a deviation (Y), which may be the distance between the position of the displayed light 140 on the target 136 and a position on the target 136 corresponding to the position of the light source 124 from which the displayed light 140 is provided. Further, the deviation (Y) can be the distance between the position on the target 136 corresponding to the position of the light source 124 from which the displayed light 140 is provided and a centroid 170 of the displayed light 140 on the target 136, as is illustrated in FIG. 12. The centroid is a point which defines the geometric center of an object. In addition, as is illustrated in FIG. 12, the deviation (Y) in locations can be the distance between a centroid 174 of a position on the target 136 corresponding to the position of the light source 124 from which the displayed light 140 is provided and a centroid 170 of the displayed light 140 on the target 136. The cell angle (β) for the group 142 of the cells 110 can then be presented in an equation below.

$$\beta = \arctan(Y/Z) \quad (1)$$

In one example, if Z is equal to 2 m and Y is equal to 3.5 mm, the cell angle (β) is about 0.1 degrees. It is understood that equation (1) shows the deviation (Y) of the light projecting through and out of the group 142 of the cells 110 only in z-direction, while the deviation of the light 140 displayed on the target 136 is not limiting, as the deviation can occur, for example, in both x and z directions. In addition, a location of the centroid 174 of a position on the target 136 corresponding to the position of the light source 124 from which the displayed light 140 is provided may be known within a range less than or equal to about 0.5 mm.

Figure 10:
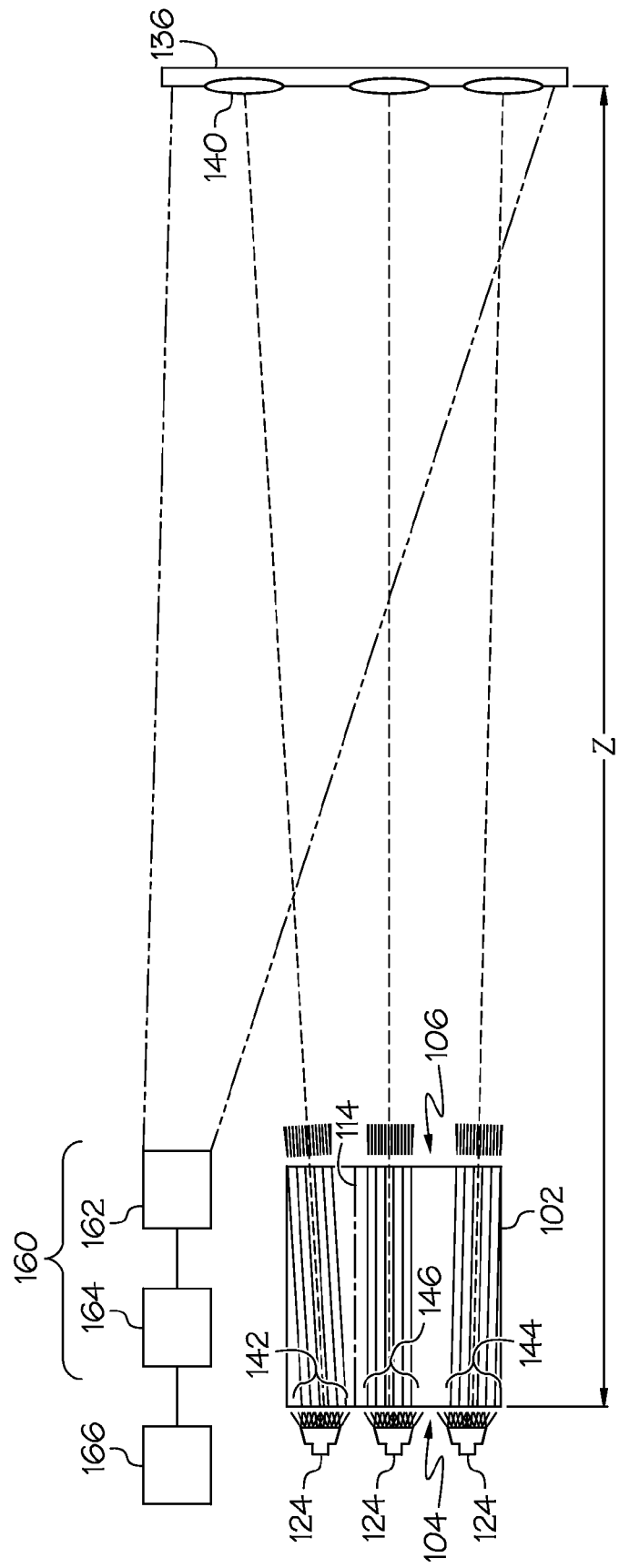
FIG. 10 is a schematic view illustrating an example of a system for inspecting a body in accordance with an embodiment.

In the example illustrated in FIG. 10, in addition to the light sources 124 and the target 136, an imaging system 160 and a system processor 166 is illustrated. The imaging system 160 may determine at least one location of the displayed light 140 on the target 136. In an example, the imaging system 160 can gather data related to a surface of the target 136 and determine a location of the displayed light 140 of the target 136 or a location of a centroid 170 of the displayed light 140 of the target 136. In one example, the digital imaging sensor 162 can sense and/or capture at least one of the shape, size, color or centroid of the light displayed on the target 136. The imaging system 160 may include a digital imaging sensor 162, such as, but not limited to, a charge-coupled device (CCD) image sensor or a complementary metal-oxide semiconductor (CMOS) image sensor. The digital imaging sensor 162 can further include any image capturing device that can be operable in the visible spectrum range.

Figure 11:
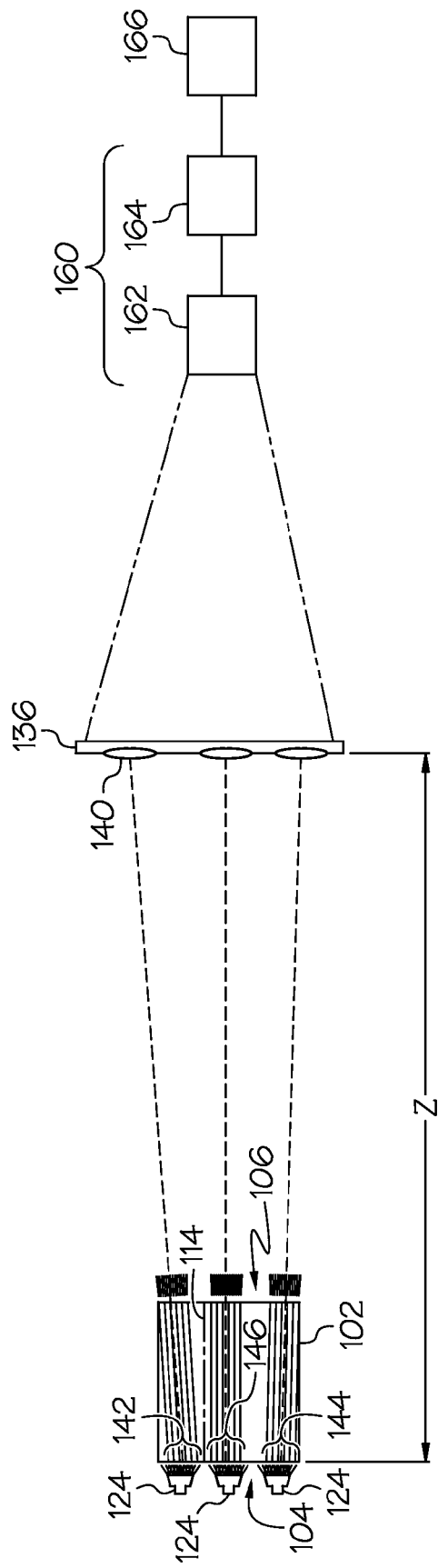
FIG. 11 is a schematic view illustrating another example of a system for inspecting the body in accordance with an embodiment.

The digital imaging sensor 162 can be positioned on either side of the target 136. For example, the digital imaging sensor 162 can be positioned on a side of the target 136 on which the body 102 is positioned, as is illustrated in FIG. 10. In this case, the digital imaging sensor 162 may be positioned either above or below the body 102. In FIG. 10, the digital imaging sensor 162 is illustrated as being positioned above the body 102. The digital imaging sensor 162 can also be positioned on a side of the target 136 that is opposite to the side of the target 136 on which the body 102 is positioned, as is illustrated in FIG. 11. In this case, the target 136 can include semi-transparent material so that the location of the displayed light 140 on the target 136 can be determined by the imaging system 160. Alternately, the digital imaging sensor 162 may be positioned to the left or right side of the body 102, as long as the digital imaging sensor 162 senses the light 140 displayed on the target 136.

The imaging processor 164 may be operably coupled to the digital imaging sensor 162 for gathering the data associated with the displayed image 140 on the target 136. The imaging processor 164 may include memory or other storage devices where one or more software or programs may be stored for gathering the data associated with the displayed light 140 on the target 136. In one example, the software or programs may include one or more coordinate systems.

Based on the gathered data using the digital imaging sensor 162, the imaging processor 164 can determine the location of the displayed light 140 on the target 136, as well as at least one of the shape, size or color of the displayed light 140 on the target 136. In an example, the imaging processor 164 can determine the position of the centroid 170 of the displayed light 140 on the target 136, as illustrated in FIG. 12, by using coordinate systems or other programs stored in the imaging processor 164.

The location of the displayed light 140 with respect to a position on the target 136 corresponding to the position of the light source 140 from which the displayed light 140 is provided can be determined using one of a number of coordinate systems. Non-limiting examples of the coordinate system can include Cartesian coordinate systems or polar coordinate systems. As such, coordinate systems can determine the location of the displayed light 140 and a position on the target 136 corresponding to the position of the light source 124 from which the displayed light 140 is provided with respect to the origin of the coordinate system used. For example, the coordinate system can be configured to determine a location of a centroid 174 of a position on the target 136 corresponding to the position of the light source 124 from which the displayed light 140 is provided the location of the centroids of the light source 124 and a location of the centroid 170 of the displayed light 140 on the target 136.

While the examples illustrated in FIGS. 5 and 9-11 show the body 102 as being relatively aligned with the light sources 124 and the target 136, no precise initial angular alignment is required between the body 102 and the various components of the system. For example, a measurement can be made by the imaging system 160 as long as the displayed light 140 are located on the target 136 within the field of view of the imaging system 160. Thus, the measurement made by the imaging system 160 may not require an alignment of the body 102 with the various components of the system by removing a tip and a tilt of the body 102 with respect to the various components of the system. Initial variations in tip and tilt of the body 102 of up to +/−10 degrees may be acceptable.

In addition, while in the examples illustrated in FIGS. 10 and 11 show the digital imaging sensor 162 and the imaging processor 164 as separate components, it is understood that both the digital imaging sensor 162 and the imaging processor 164 can be integrated into each other. For example, the digital imaging sensor 162 may be configured to include the imaging processor 164.

The system processor 166 may compare the determined location of the displayed light 140 with a location of the light source 124 and calculate, from the comparison thereof, a pointing angle or vector for a group 142 of the cells 110 corresponding to the light source 124. In an example, the system processor 166 can compare the determined location of the centroid 170 of the displayed light 140 with a location of the light source 124 and calculate, from the comparison thereof, the pointing angle or vector for a group 142 of the cells 110 corresponding to the light source 124.

The system processor 166 may be operably coupled to the imaging system 160 for receiving the location of the displayed light 140 on the target 136. The system processor 166 can include one or more memory or other storage devices where one or more software or programs may be stored for executing one or more numerical calculations for comparing the determined location of the displayed light 140 with a location of the light source 124. For this, one or more software or program in the system processor 166 can include the use of the aforementioned coordinate systems for comparing the location of the displayed light 140 determined by the imaging system 160 with the location of the light source 124 corresponding with the displayed light 140. The software or programs stored in the system processor 166 can further calculate the location of the displayed light 140 with respect to the location of corresponding light source 124 in terms of a pointing angle or a pointing vector.

While the system processor 166 and the imaging system 160 are illustrated in FIGS. 10 and 11 as being separate, both the system processor 166 and the imaging system 160 can be integrated into each other. For example, the system processor 166 may be configured to include the imaging system 160, which in turn can include the digital imaging sensor 162 and the imaging processor 164. As such, the digital imaging sensor 162, the imaging processor 164 and the system processor 166 can be integrated into one system.

FIG. 12 illustrates an example of locations of centroids 170 of the displayed light 140 with respect to locations of centroids 174 of the light sources 124 respectively corresponding to the centroids 170 to calculate at least one of the pointing angle and the pointing vector for corresponding groups 118 of the cells 110 of the body 102. As shown in the example illustrated in FIG. 12, dotted circles represent the locations of the light sources 124, and solid circles represent the locations of the displayed light 140 corresponding with the light sources 124. The locations of the displayed light 140 do not necessarily coincide with the locations of the corresponding light sources 124. Further, the deviation of the location of each displayed light 140 from the location of the corresponding light source 124, in terms of the pointing angle or the pointing vector, can vary from one light source to another light source. This implies that cells 110 extending from the first end side 104 to the second end side 106 of a body 102, such as the body 102 illustrated in FIGS. 5 and 9-11 are not necessarily parallel to the longitudinal axis 114 of the body 102.

Multiple light sources 124 can be simultaneously operated to project light through and out of corresponding multiple groups 118 of the cells 110 of the body 102. As a result, the light projected through and out of the multiple groups 118 of the cells 110 can be simultaneously displayed on the target 136. As such, the multiple locations of the displayed light 140 on the target 136 can be simultaneously determined by the imaging system 160. For example, the multiple locations of the centroids 170 of the displayed light 140 can be simultaneously determined by the imaging system 160.

Alternatively, the imaging system 160 can identify a particular plurality of the locations of the displayed light 140 from the multiple locations of the displayed light 140. In one example, only one location of the displayed light 140 is determined by the imaging system 160. In another example, all locations of the displayed light 140 are identified. The number of locations of the displayed light 140 can be determined by the imaging system 160. Alternatively, the number of locations of the displayed light 140 can be identified by the system processor 166.

When multiple locations of the displayed light 140 are identified, each of the multiple locations can be compared with multiple corresponding locations of the light sources 124 using the system processor 166. The multiple locations of the light sources 124 correspond to the multiple locations of the displayed light 140 in that the displayed light 140 is, in fact, displayed as a result of the light emitted from the corresponding light sources 124 that is projected through and out of multiple corresponding groups 118 of the cells 110.

The system processor 166 can further calculate the pointing angle or the pointing vector for each of the multiple groups 118 of the cells 110. For example, as is illustrated in FIG. 12, the pointing angle of the displayed light 140 with respect to the corresponding light source 124 can be represented as al, and the distance from the displayed light 140 to the corresponding light source 124 from which the displayed light 140 is provided can be represented as R1, both of which can be calculated by the system processor 166 by comparing the location of the displayed light 140 and the location of the corresponding light source 124 from which the displayed light 140 is provided.

In general, the numerical value for $\alpha 1$ and R1 can represent the degree of tilt for the group of the cells in the body 102. For example, variations in the pointing angle $\alpha 1$ may correspond to variations in the cell angle ($\beta$) of the group 118 of the cells 110. In another example, the distance R1 may correspond to a degree of tilting.

The pointing angle $\alpha 1$ of the displayed light 140 with respect to the corresponding light source 124 and the pointing vector of the group 142 of the cells 110 can be used when the pointing angle and the pointing vector are calculated for multiple groups of the cells over multiple regions of the body 102. In an example, the pointing angle $\alpha 1$ and the pointing vector can be used in suggesting how the body 102 should be skinned. For example, a particular outer portion of the body 102 can be ground along a predetermined direction by a predetermined depth based on the pointing angle $\alpha 1$ and the pointing vector of a particular group 118 of the cells 110 to minimize cells 110 in the particular outer portion of the body 102 that may be blocked by a grinding and skinning procedure.

With respect to the example illustrated in FIG. 8, the pointing angle $\alpha 1$ or the pointing vector for the initial group 118 of the cells 110 corresponding with the displayed light 140 can be calculated from the comparison of the location of the displayed light 140 and the location of the corresponding light source 124 from which the displayed light 140 is provided. For example, the pointing angle $\alpha 1$ or the pointing vector for the initial group 118 of the cells 110 corresponding with the displayed light 140 can be calculated from the comparison of the location of the centroid 170 of the displayed light 140 and the location of the corresponding light source 124 from which the displayed light 140 is provided. In an example, the location of the corresponding light source 124 is defined by a centroid 174 of the corresponding light source 124.

By moving the light source 124 and repeating the steps of projecting of light through and out of a group 118 of the cells 110, displaying the light 140 on the target 136, determining the location of the displayed light 140, comparing the determined location of the displayed light 140 and the location of the corresponding light source 124, and calculating one of the pointing angle and the pointing vector for the group 118 of the cells 110 of the body 102, the example illustrated in FIG. 8 having one light source 124 can obtain multiple instances of displayed light 140 corresponding with multiple groups 118 of the cells 110 in the same way as a system that includes multiple light sources projecting light through and out of multiple groups 118 of the cells 110 simultaneously.

While it was assumed in the above-referenced example illustrated in FIG. 8 that only one light source 124 moves along a predetermined path to project light through and out of the body 102 for inspecting the body 102, it is also understood that multiple light sources 124 can also move along the predetermined path for inspecting the body 102. In one example, two light sources 124 can move along the predetermined path, with the first light source 124 projecting light through and out of the groups 118 of the cells 110 in an upper half portion of the body 102, and the second light source 124 projecting light through and out of the groups 118 of the cells 110 in a lower half portion of the body 102.

It is noted that the arrangement as illustrated in FIG. 12 does not intend to be limiting, as various other arrangements of the light sources 124 are possible in accordance with aspects of the disclosure. It is also understood that a graphic view as illustrated in FIG. 12 can be constructed by the system processor 166 to provide a user with visual information about locations of displayed light 140 with respect to the locations of the corresponding light sources 124 from which the displayed light 140 is provided. Alternately, the user may be provided with numerical information only about the locations of one or more groups 118 of the cells 110.

Figure 13:
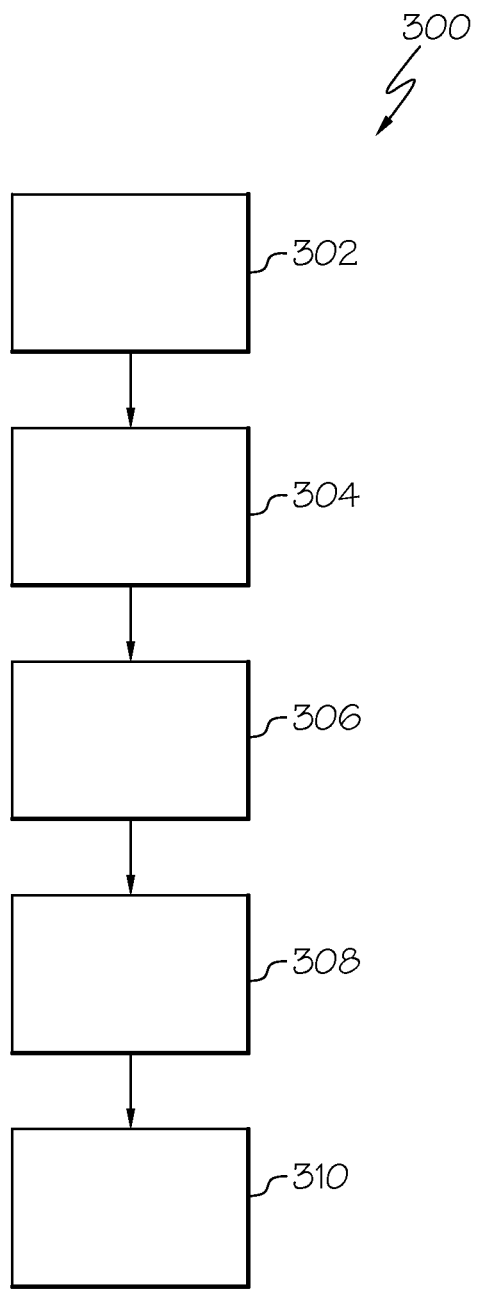
FIG. 13 is a schematic view illustrating an example of a method of inspecting a body in accordance with an embodiment.

FIG. 13 is a schematic view illustrating an example of a method 300 of inspecting a body 102. It may be understood that the sequence of steps depicted in FIG. 13 is for illustrative purposes only, and is not meant to limit the method in any way as it is understood that the steps may proceed in a different logical order, additional or intervening steps may be included, or described steps may be divided into multiple steps, without detracting from the disclosure. The method 300 in FIG. 13 may be incorporated into a cycle of operation for the manufacturing of the body 102, such as prior to, during or after the manufacturing of the body 102. Alternatively, the method 300 in FIG. 13 may also be a stand-alone process.

The method 300 includes the step 302 of projecting light through and out of at least one group 118 of the cells 110 from at least one corresponding light source 124. The light to be projected from the corresponding light source 124 can include diffuse light. One or more light sources 124 can be stationary with respect to the body 102. Alternatively, one or more light sources 124 can be configured to move along a predetermined path in at least one of x, y, and z directions with respect to the body 102 or vice versa.

The method 300 also includes the step 304 of displaying the light projected through and out of the at least one group 118 of the cells 110 on the target 136. The target 136 can be one of semi-transparent and opaque. One or more beams of light projected from the corresponding light sources 124 through and out of the corresponding groups 118 of the cells 110 can be simultaneously displayed on the target 136. Alternately, one or more beams of light projected from the corresponding light sources 124 through and out of the corresponding groups 118 of the cells 110 can be consecutively displayed one at a time on the target 136 when the one or more light sources 124 are moved along a predetermined path.

The method 300 can further include the step 306 of determining at least one location of the displayed light 140. The at least one location of the displayed light 140 can be determined by the imaging system 160. The imaging system 160 can include memory or other storage devices that include software or programs for determining the location of the displayed light 140. In one example, the software or programs may include coordinate systems for determining the location of the displayed light 140 on the target 136.

The method 300 can further include the step 308 of comparing the determined at least one location of the displayed light 140 with a location of the at least one corresponding light source 124 by the system processor 166. The system processor 166 can include memory or a storage device that may include software or programs. In one example, the location of the centroid 170 of the displayed light 140 on the target 136 can be compared with the location of the centroid 174 of the corresponding light source 124 from which displayed light 140 originates. The method 300 can further include the step 310 of calculating, from the location comparison of the at least one location of the displayed light 140 with the location of the at least one corresponding light source 124, at least one of the pointing angle and the pointing vector for each group 118 of the cells 110. While steps 308 and 310 are separately described, it is understood that steps 308 and 310 can occur substantially at the same time in the system processor 166.

Various modifications and variations can be made to the embodiments described herein without departing from the spirit and scope of the claimed subject matter. Thus, it is intended that the specification cover the modifications and variations of the embodiments described herein provided such modifications and variations come within the scope of the appended claims and their equivalents. It will be apparent to those skilled in the art that various modifications and variations can be made without departing from the spirit and scope of the claims.

What is claimed is:

1. A system for inspecting a body, the body comprising a first end side, a second end side, and cells extending through the body from the first end side to the second end side, the system comprising:
   at least one light source configured to project light through and out of at least one corresponding group of the cells;
   a target configured to display the light projected through and out of the at least one corresponding group of the cells, wherein the target is configured to distinguish the light displayed on the target from the remaining portion of the target;
   a digital imaging sensor configured to determine at least one location of the displayed light on the target by sensing the light scattered from the target; and
   a system processor configured to compare the determined at least one location of the displayed light with a location of the at least one light source and calculate, from the comparison thereof, at least one of a pointing angle and a pointing vector for the at least one corresponding group of the cells.

2. The system of claim 1, wherein the at least one light source is a diffuse light source.

3. The system of claim 1, wherein the target is one of semi-transparent and opaque.

4. The system of claim 1, wherein the digital imaging sensor is further configured to gather data related to a surface of the target and determine a location of a centroid of the displayed light from the gathered data.

5. The system of claim 4, wherein the system processor is further configured to compare the determined location of the centroid with the location of the at least one light source and calculate, from the comparison thereof, the at least one of the pointing angle and the pointing vector for the at least one corresponding group of the cells.

6. The system of claim 1, wherein the at least one light source is one of multiple light sources configured to project light through and out of multiple corresponding groups of the cells, the at least one corresponding group of the cells being one of the multiple corresponding groups of the cells,
   wherein the target is further configured to display the light projected through and out of the multiple corresponding groups of the cells,
   wherein the digital imagining sensor is further configured to determine multiple locations of the displayed light on the target by sensing the displayed light scattered from the target, the at least one location of the displayed light on the target being one of the multiple locations of the displayed light on the target, and wherein the system processor is further configured to compare the determined multiple locations of the displayed light with respective locations of the multiple light sources and calculate, from the comparison thereof, at least one of the pointing angle and the pointing vector for the multiple corresponding groups of the cells.

7. The system of claim 6, wherein the multiple light sources are further configured to project the light simultaneously.

8. The system of claim 1, wherein, after the system processor calculates the at least one of the pointing angle and the pointing vector for the at least one corresponding group of the cells, the at least one light source is moved to project light through and out of another corresponding group of the cells.

9. A method for inspecting a body, the body comprising a first end side, a second end side, and cells extending through the body from the first end side to the second end side, the method comprising:
projecting light through and out of at least one group of the cells from at least one corresponding light source;
displaying the light projected through and out of the at least one group of the cells on a target, wherein the target is configured to distinguish the light displayed on the target from the remaining portion of the target;
sensing the light scattered from the target to determine at least one location of the displayed light;
comparing the determined at least one location of the displayed light with a location of the at least one corresponding light source projecting the light; and
calculating, from the location comparison thereof, at least one of a pointing angle and a pointing vector for each of the at least one group of the cells.

10. The method of claim 9, wherein the projecting of the light comprises projecting diffuse light.

11. The method of claim 9, wherein the displaying of the light comprises displaying the light on the target that is one of semi-transparent and opaque.

12. The method of claim 9, wherein the displaying of the light comprises displaying the light on the target, and
wherein the determining of the at least one location comprises gathering data related to a surface of the target and determining a location of a centroid of the displayed light from the gathered data.

13. The method of claim 12, wherein the comparing of the locations comprises comparing the determined location of the centroid with the location of the at least one corresponding light source, and
wherein the calculating of the at least one of the pointing angle and the pointing vector comprises calculating, from the comparing of the determined location of the centroid with the location of the at least one corresponding light source, the at least one of the pointing angle and the pointing vector for the at least one group of the cells.

14. The method of claim 9, wherein the determining of the at least location is performed by a digital imaging sensor.

15. The method of claim 9, wherein the projecting of the light comprises projecting the light through and out of multiple groups of the cells from multiple corresponding light sources, the at least one group of the cells being one of the multiple groups of the cells, the at least one corresponding light source being one of the multiple corresponding light sources,
wherein the displaying of the light comprises displaying the light projected through and out of the multiple groups of the cells on the target,
wherein the determining of the at least one location comprises determining multiple locations of the displayed light, the at least one location of the light being one of the multiple locations of the displayed light,
wherein the comparing of the determined at least one location comprises comparing the determined multiple locations of the displayed light with locations of the multiple corresponding light sources, and
wherein the calculating comprises calculating, from the location comparison thereof, at least one of the pointing angle and the pointing vector for the multiple groups of the cells.

16. The method of claim 15, wherein the projecting of the light through and out of two or more of the groups of the cells is simultaneous.

17. The method of claim 9, further comprising, after the calculating of the at least one of the pointing angle and the pointing vector:
moving the at least one corresponding light source; and
repeating the projecting, the displaying, the determining, the comparing, and the calculating for another group of the cells.

18. A system for inspecting a body, the body comprising a first end side, a second end side, and cells extending through the body from the first end side to the second end side, the system comprising:
multiple light sources configured to simultaneously project light through and out of multiple corresponding groups of the cells;
a target configured to display the light simultaneously projected through and out of the multiple corresponding groups of the cells in multiple regions respectively corresponding with the multiple groups of the cells, wherein the target is configured to distinguish the light displayed on the target from the remaining portion of the target;
an imaging system configured to determine respective centroids of the multiple regions on the target by sensing the light scattered from the target; and
a system processor configured to compare locations of the respective centroids of the multiple regions with respective locations of the multiple light sources and calculate, from the comparison thereof, at least one of a pointing angle and a pointing vector for the multiple corresponding groups of the cells.

19. The system of claim 18, wherein the imaging system comprises an imaging device comprising a digital imaging sensor, the imaging device being configured to gather data from the displayed light reflecting from a surface of the target facing the multiple corresponding groups of the cells.

20. The method of claim 9, wherein the displaying the light on the target comprises displaying dispersed light.

* * * * *